US006218586B1

(12) United States Patent
Takada et al.

(10) Patent No.: US 6,218,586 B1
(45) Date of Patent: Apr. 17, 2001

(54) METHOD FOR PREPARING PERHALOGENATED FIVE-MEMBERED CYCLIC COMPOUND

(75) Inventors: Naoto Takada; Masatomi Kanai; Hideaki Imura; Takeo Komata, all of Saitama (JP)

(73) Assignees: Central Glass Company, Limited, Ube; Nippon Zeon Co., Ltd., Tokyo, both of (JP)

( * ) Notice: Subject to any disclaimer, the term of this patent is extended or adjusted under 35 U.S.C. 154(b) by 0 days.

(21) Appl. No.: 09/434,277

(22) Filed: Nov. 5, 1999

(30) Foreign Application Priority Data

Nov. 5, 1998  (JP) .................................. 10-314661
Nov. 30, 1998 (JP) .................................. 10-339420

(51) Int. Cl.⁷ .................................................. C07C 17/08
(52) U.S. Cl. ........................ 570/165; 570/166; 570/167; 570/168; 570/169
(58) Field of Search ..................... 570/165, 166, 570/167, 168, 169

(56) References Cited

U.S. PATENT DOCUMENTS

| 2,449,233 | 9/1948 | Kischitz . | |
|---|---|---|---|
| 2,459,783 | 1/1949 | McBee . | |
| 3,149,170 | 9/1964 | Clark . | |
| 3,178,482 | 4/1965 | Baranauckas . | |
| 3,258,500 | 6/1966 | Swamer . | |
| 5,264,639 | * 11/1993 | Morikawa et al. | 570/168 |
| 5,416,246 | 5/1995 | Krespan et al. | 570/151 |

FOREIGN PATENT DOCUMENTS

| 1543015 | 3/1972 | (DE) . |
|---|---|---|
| 3935493 A1 | 10/1989 | (DE) . |
| 425888 | 5/1991 | (EP) . |
| 768289 | 4/1997 | (EP) . |
| 913380 | 5/1999 | (EP) . |
| 3-151336 | 6/1991 | (JP) . |
| 8-333285 | 12/1996 | (JP) . |
| WO 97 43233 | 11/1997 | (WO) . |
| WO 99 14173 | 3/1999 | (WO) . |

OTHER PUBLICATIONS

Henne et al., "Flourinated Derivatives of Cyclopentene and Cyclopentane". *J. Am. Chem. Soc.* 67:1235–1237 (1945).
Bardin et al., "Fluorination of Polyhalogenated Unsaturated Compounds with Vanadium Pentafluoride". *J. of Flourine Chem.* 49:385–400 (1990).
Newcomer et al., "The Chemical Behavior of Hexachloro-cyclopentadiene. I. Transformation to Octachloro–3a,4,7,7a–Tetrahydro–4,7–methanoindene–1,8–dione". *J. Am. Chem. Soc.* 71:946–951 (1949).

* cited by examiner

*Primary Examiner*—Alan Siegel
(74) *Attorney, Agent, or Firm*—Evenson, McKeown, Edwards & Lenahan, P.L.L.C.

(57) ABSTRACT

The invention relates to a method for preparing a fluorinated product that is a first perhalogenated five-membered cyclic compound (e.g., 1,2-dichlorohexafluorocyclopentene and 1,1-dichlorooctafluorocyclopentane). This method includes reacting in a gas phase a starting material that is a second perhalogenated five-membered cyclic compound having at least one unsaturated bond, at substantially the same time with chlorine and hydrogen fluoride, in the presence of a fluorination catalyst containing an activated carbon optionally carrying thereon a metal compound, thereby to decrease the number of the at least one unsaturated bond and to increase the number of fluorine atoms of the second compound. The method is appropriate for the production of the first perhalogenated five-membered cyclic compound in an industrial scale.

21 Claims, No Drawings

US 6,218,586 B1

METHOD FOR PREPARING PERHALOGENATED FIVE-MEMBERED CYCLIC COMPOUND

BACKGROUND OF THE INVENTION

The present invention relates to methods for preparing perhalogenated five-membered cyclic compounds, such as chlorofluorocyclopentenes and chlorofluorocyclopentanes, particularly 1,2-dichlorohexafluorocyclopentene, 1,1-dichlorooctafluorocyclopentane and the like, which are useful as intermediates for heptafluorocyclopentane and as intermediates for various fluorine-containing compounds. Heptafluorocyclopentane is useful as a fluorine-containing detergent, a fluorine-containing drying solvent, or the like.

It is known that hydrogen-containing fluorinated cyclopentanes are produced at first by fluorinating chlorinated cycloalkenes corresponding to the fluorinated cyclopentanes to obtain vicinally chlorinated fluorocyclopentene derivatives, and then by fluorinating and hydrogenating these derivatives. It is known that vicinally chlorinated fluorocyclopentene derivatives are produced by a first method, in which perhalogenated cycloolefins are used as starting materials, or a second method, in which perhalogenated cycloconjugated dienes are used as starting materials. In either of these first and second methods, the fluorination can be conducted by either a liquid phase process or a gas phase process. This liquid phase process can be conducted by using antimony trifluoride or hydrogen fluoride as a fluorination agent, in the presence of an antimony halide as a fluorination catalyst. Antimony halide is, however, highly corrosive. Furthermore, if hydrogen fluoride is used as the fluorination catalyst in an industrial scale production, the reaction pressure may become as high as 10–30 kg/cm². This may cause some limitations in the selection of devices. The gas phase process can be conducted by using hydrogen fluoride as a fluorination agent, in the presence of a fluorination agent selected from various substances. U.S. Pat. No. 3,178,482 discloses a method for producing 1,2-dichlorohexafluorocyclopentene by fluorinating trichloropentafluorocyclopentene in the presence of activated carbon as catalyst. U.S. Pat. No. 3,258,500 discloses a method for producing 1,2-dichlorohexafluorocyclopentene by fluorinating 1,2,4-trichloropentafluorocyclopentene in the presence of chromium oxide ($CrO_3$) as catalyst. DE 1543015 discloses a method for producing 1,2-dichlorohexafluorocyclopentene by fluorinating octachlorocyclopentene in the presence of a Cu/Al oxide.

It is disclosed in J. Am. Chem. Soc., 67, 1235 (1945) to react 1,2-dichlorohexafluorocyclopentene with chlorine at 70° C. under the UV light irradiation in order to saturate its double bond with a halogen except fluorine. It is disclosed in J. of Fluorine Chem., 49(3), 385–400 (1990) to produce 1,2 dichlorooctafluorocyclopentane by fluorinating 1,2-dichlorohexafluorocyclopentene at 25° C. in the presence of vanadium pentachloride. Japanese Patent First Publication JP-A-8-333285 discloses a method for producing 1,2-dichlorohexafluorocyclopentene at first by reacting hexachlorocyclopentadiene with chlorine in the presence of antimony trichioride, thereby to respectively convert the hexachlorocyclopentadiene and antimony trichloride to octachlorocyclopentene and antimony pentachloride, and then by adding hydrogen fluoride thereto. JP-A-3-151336 discloses a method for fluorinating hexachlorocyclopentadiene in a gas phase in the presence of chlorine and hydrogen fluoride using a Mg/Bi/Fe oxide as a catalyst, thereby to obtain 1,2-dichlorohexafluorocyclopentene. It is, however, necessary to previously fluorinate such oxides, which are disclosed in JP-A-3-151336 and U.S. Pat. No. 3,258,500, if they are used as fluorination catalysts. This fluorination takes a long time, and it is difficult to achieve a complete fluorination.

One of the aimed products of the invention, that is, 1,1-dichlorooctafluorocyclopentane, is a useful compound, since it can easily be reduced by hydrogen to beptafluorocyclopentane. A method for producing 1,1-dicholorooctafluorocyclopentane is disclosed in U.S. Pat. No. 5,416,246. In this method, it is produced through isomerization of 1,2-dichlorooctafluorocyclopentane by passing 1,2-dichlorooctafluorocyclopentane, together with hexafluoropropene, through chlorofluorinated aluminum heated at 130° C.

SUMMARY OF THE INVENTION

It is therefore an object of the present invention to provide a method for preparing a perhalogenated five-membered cyclic compound, such as 1,2-dichlorohexafluorocyclopentene or 1,1-dichlorooctafluorocyclopentane, which method is appropriate for the production of the same in an industrial scale.

According to the present invention, there is provided a method for preparing a fluorinated product that is a first perhalogenated five-membered cyclic compound. This method comprises reacting in a gas phase a starting material that is a second perhalogenated five-membered cyclic compound (e.g., perchlorocyclopentadiene or perchlorocyclopentene) having at least one unsaturated bond, at substantially the same time with chlorine and hydrogen fluoride, in the presence of a fluorination catalyst comprising an activated carbon optionally carrying thereon a metal compound, thereby to decrease the number of said at least one unsaturated bond and to increase the number of fluorine atoms of said second compound. By this reacting, it becomes possible to obtain the first perhalogenated five-membered cyclic compound with a high yield, such as chlorofluorocyclopentenes and chlorofluorocyclopentanes, particularly 1,2-dichlorohexafluorocyclopentene and 1,1-dichlorooctafluorocyclopentane. In this method, it is not necessary to use a special pressure-tight reactor nor have many reaction steps. Furthermore, the above fluorination catalyst can easily be prepared and is stable for a long time in activity.

DESCRIPTION OF THE PREFERRED EMBODIMENTS

In the invention, the fluorinated product, that is, the first perhalogenated five-membered cyclic compound, may be a first perhalogenated cyclopentene represented by the general formula $C_5Cl_DF_{8-D}$, where D is an integer of 0–7, or a perhalogenated cyclopentane represented by the general formula $C_5Cl_EF_{10-E}$, where E is an integer of 0–9. Furthermore, the starting material, that is, the second perhalogenated five-membered cyclic compound, may be a perhalogenated cyclopentadiene represented by the general formula $C_5Cl_AF_{6-A}$, where A is an integer of 0–6, or a second perhalogenated cyclopentene represented by the general formula $C_5Cl_BF_{8-B}$, where B is an integer of 0–8. As stated above, the fluorinated product is less than the starting material in the number of unsaturated bonds in the molecule.

As mentioned above, the fluorinated product is greater than the starting material in the number of fluorine atoms in the molecule. Therefore, in case that the starting material is the perhalogenated cyclopentadiene represented by the general formula $C_5Cl_AF_{6-A}$, where A is an integer of 0–6, and the fluorinated product is the first perhalogenated cyclopentene represented by the general formula $C_5Cl_DF_{8-D}$, where D is an integer of 0–7, A and D are such that the expression D<(2+A) is satisfied. Similarly, in case that the starting material is the perhalogenated cyclopentadiene represented by the general formula $C_5Cl_AF_{6-A}$, where A is an integer of 0–6, and the fluorinated product is the perhalogenated cyclopentane represented by the general formula $C_5Cl_EF_{10-E}$, where E is an integer of 0–9, A and E are such that the expression E<(4+A) is satisfied. Similarly, in case that the starting material is the second perhalogenated cyclopentene represented by the general formula $C_5Cl_BF_{8-B}$, where B is an integer of 0–8, and the fluorinated product is the perhalogenated cyclopentane represented by the general formula $C_5Cl_EF_{10-E}$, where E is an integer of 0–9, B and E are such that the expression E<(2+B) is satisfied.

As mentioned above, the starting material is reacted with chlorine and hydrogen fluoride at substantially the same time. This timing of "at substantially the same time" means that the reaction is conducted under a condition that both chlorine and hydrogen fluoride are present in a single reaction system prepared by supplying these to this reaction system. It is, however, optional to conduct the reaction under an analogous condition, in which both chlorine and hydrogen fluoride become present in a single reaction system only if the average of a period of time is taken, by intermittently supplying chlorine and hydrogen fluoride to the reaction system. In other words, the timing of "at substantially the same time" may include this analogous condition.

One starting material of the invention, that is, the perhalogenated cyclopentadiene represented by the general formula $C_5Cl_AF_{6-A}$, where A is an integer of 0–6, may be, for example, perchlorocyclopentadiene. The method for producing perchlorocyclopentadiene is not particularly limited. For example, it can be obtained by heating pentane, isopentane, cyclopentane or the like, together with chlorine, at a temperature of 300–430° C., on acid clay or another surface-active substance, followed by heating at a temperature of 450–525° C.

Another starting material of the invention is the second perhalogenated cyclopentene represented by the general formula $C_5Cl_BP_{8-B}$, where B is an integer of 0–8. In this cyclopentene, the number of chlorine atoms may vary from 0 to 8, and that of fluorine atoms may vary from 0 to 7. These halogen atoms may be bonded to any carbon atoms. This cyclopentene is not limited to a particular compound(s). Examples of this cyclopentene are 1-chloroheptafluorocyclopentene, 1,2-dichlorohexafluorocyclopentene, 1,2,3-trichloropentafluorocyclopentene, 1,2,4-trichloropentafluorocyclopentene, 1,2,3,4-tetrachlorofluorocyclopentene, 1,2,3,4,4-pentachlorotrifluorocyclopentene, hexachlorodifluorocyclopentene, hexachlorodifluorocyclopentene, beptachlorofluorocyclopentene, and octachlorocyclopentene. Of these, 1,2-dichlorohexafluorocyclopentene is the most preferable. The second perhalogenated cyclopentene may be prepared by a conventional method. In connection with this, Newcomer; McBee, J. Amer. Chem. Soc., 71 (1949) 946, 950 discloses a method for producing octachlorocyclopentene by chlorinating hexachlorocyclopentadiene with chlorine using a metal chloride as a catalyst. Furthermore, Henne et al., J. Am. Chem. Soc., 67, 1235 (1945) discloses a reaction of octachlorocyclopentene with a mixture of antimony trifluoride and antimony trifluorodichloride, thereby to obtain 1,2-dichlorohexafluorocyclopentene, 1,2,4-trichloropentafluorocyclopentene, and 1,2,3,4-tetrachlorotetrafluorocyclopentene.

One fluorinated product of the invention is the first perhalogenated cyclopentene represented by the general formula $C_6Cl_DF_{8-D}$, where 15 is an integer of 0–7. In this cyclopentene, the number of chlorine atoms may vary from 0 to 7, and that of fluorine atoms may vary from 1 to 8. These halogen atoms may be bonded to any carbon atoms. Examples of this cyclopentene are octafluorocyclopentene, 1-chloroheptafluorocyclopentene, 1,2-dichlorohexafluorocyclopentene, 1,2,4-trichloropentafluorocyclopentene, 1,2,3-trichloropentafluorocyclopentene, 1,2,3,4-tetrachlorotetrafluorocyclopentene, 1,2,3,4,4-pentachlorotrifluorocyclopentene, hexachlorodifluorocyclopentene, hexachlorodifluorocyclopentene, and heptachlorofluorocyclopentene. Of these, 1,2-dichlorohexafluorocyclopentene is the most preferable.

Another fluorinated product of the invention is the perhalogenated cyclopentane represented by the general formula $C_5Cl_EF_{10-E}$, where E is an integer of 0–9. Preferable examples of this cyclopentane are 1,1,2,2-tetrachlorohexafluorocyclopentane, 1,1,2-trichloroheptafluoropentane, 1,1-dichlorooctafluorocyclopentane, 1,2-dichlorooctafluorocyclopentane, chlorononafluorocyclopentane and decafluorocyclopentane. Of these, 1,1-dichlorooctafluorocyclopentane is particularly preferable.

The fluorination catalyst used in the invention comprises an activated carbon optionally carrying thereon a metal compound. This metal compound contains at least one metal selected from metals of 4, 5, 6, 7, 9, 10, 11, 14 and 15 groups of periodic table. Preferable examples of the at least one metal are manganese, cobalt, nickel, molybdenum, niobium, copper, antimony, titanium, tin and tantalum. Of these, molybdenum, niobium, tantalum and antimony are more preferable examples In the invention, the activated carbon, which is used as a carrier of the fluorination catalyst or the fluorination catalyst itself, is not limited to a particular type. The activated carbon may be prepared from a vegetable raw material such as wood, sawdust, charcoal, coconut husk coal, palm core coal, or raw ash; a coal such as peat, lignite, brown coal, bituminous coal, or anthracite; a petroleum raw material such as petroleum residue, sulfuric sludge, or oil carbon; or a synthetic resin raw material. The activated carbon may be selected from various commercial activated carbons. Examples of commercial activated carbons that are usable in the invention are an activated carbon having a trade name of CALGON GRANULAR ACTIVATED CARBON CAL that is made of bituminous coal and made by TOYO CALGON CO. and a coconut husk coal made by Takeda Chemical Industries, Ltd. An activated carbon used in the invention is generally in the form of granules. Its shape and size are not particularly limited, and may be decided depending on the reactor's size. It is preferable that the activated carbon used in the invention has a large specific surface area. Commercial products of activated carbon will suffice for the invention with respect to specific surface area and micropore volume. In the invention, the specific surface area of the activated carbon is preferably greater than 400 $m^2/g$, more preferably from 800 to 3,000 $m^2/g$. Furthermore, the micropore volume of the activated carbon is preferably greater than 0.1 cm³/g, more preferably from 0.2 to 1.5 cm³/g. In the invention, it is preferable to use an activated carbon prepared from a vegetable raw material such as wood, sawdust, charcoal, coconut husk coal, palm core coal, or raw ash. Prior to the use of the activated carbon, it is preferable to activate the surface of the activated carbon and remove ashes therefrom by immersing the activated carbon in a basic aqueous solution of ammonium hydroxide, sodium hydroxide, potassium hydroxide or the like at about room temperature for about 10 hr or more or by subjecting the activated carbon to a pretreatment with an acid such as nitric acid, hydrochloric acid or hydrofluoric acid at room temperature or under a heated condition. This pretreatment is conventionally used, upon the use of activated carbon as a catalyst carrier.

In case that the activated carbon (carrier) carries thereon a high valency metal halide, it is preferable to remove water as much as possible from the carrier by heating, vacuum or the like, prior to the application of the high valency metal halide in order to prevent deterioration of the halide caused by hydrolysis or the like. The metal of this halide can be selected from antimony, molybdenum, niobium, tantalum, and the like.

In the invention, the amount of at least one metal that is carried on the activated carbon (carrier) is preferably from 0.1 to 50 parts by weight, more preferably from 0.5 to 50 parts by weight, still more preferably from 2 to 50 parts by weight, further more preferably from 5 to 50 parts by weight, relative to 100 parts by weight of the carrier. If the amount of the at least one metal is too much, the catalyst may become powdery and thus should be handled with care.

In the invention, the method for preparing a fluorination catalyst that comprises an activated carbon (carrier) carrying thereon a metal compound is not particularly limited. In the preparation of this fluorination catalyst, the carrier, which has been subjected to the above-mentioned pretreatment, may be immersed into a solution of the metal compound or the metal compound itself, if it is in the form of liquid, or alternatively the solution or the metal compound itself may be sprayed on the carrier. Then, the carrier is dried and then brought into contact with a fluorination agent in the gas form (e.g., hydrogen fluoride and chlorofluorohydrocarbon) under a heated condition, thereby to partially or completely fluorinate the metal compound carried thereon. With this, the preparation of the fluorination catalyst is completed.

In the invention, the metal compound used for preparing the fluorination catalyst may be at least one of nitrate, chloride, organic acid salt, organic complex and the like of the at least one metal, which is soluble in a solvent such as water, ethanol, or acetone. Furthermore, the metal compound, such as oxide or hydroxide, or the elemental metal may be dissolved in a mineral acid, such as hydrochloric acid or nitric acid, in the preparation of the fluorination catalyst. Nonlimitative examples of the metal compound are manganese nitrate, manganese chloride, manganese dioxide, manganese acetate, nickel nitrate, nickel chloride, nickel acetate, cobalt nitrate, cobalt chloride, molybdenum chloride, niobium chloride, copper nitrate, copper chloride, antimony pentachloride, antimony trichloride, antimony pentafluoride, titanium tetrachloride, titanium trichloride, tin tetrachloride, and tantalum pentachloride.

In the invention, a fluorination catalyst having the activated carbon (carrier) carrying thereon a halide of a metal of high valence, such as antimony, molybdenum, niobium, tantalum, titanium or tin, can be prepared as follows. For example, such halide itself, if it is in the form of liquid at room temperature, is gradually added to an activated carbon that has been subjected, according to need, to a pretreatment such as desiccation, acid treatment and the like. Alternatively, the activated carbon is immersed in a solution, in which such halide is dissolved in an inert solvent, followed by heating and/or vacuum. Examples of this inert solvent are chlorinated solvents such as carbon tetrachloride, chloroform, methylene chloride, tetrachloroethylene, trichloroethylene, and tetrachloroethane; fluorochlorinated solvents such as 2,2-dichloro 1,1,1-trifluoroethane, 1,1,-dichloro 1-fluoroethane, 3,3-dichloro-1,1,1,2,2-pentafluoropropane, and 1,3-dichloro-1,1,2,2,3-pentafluoropropane; and alcohols such as methanol, ethanol and isopropanol. Antimony compounds are relatively easily oxidized. Thus, it is optional to immerse the carrier in a solution, in which a halide of a metal of low valence, such as antimony trichloride, is dissolved in the above-mentioned inert solvent, and then turn this halide into a pentavalent halide, for example, by chlorine. In the invention, a halide of high valence metal may be antimony pentachloride, antimony pentafluoride, molybdenum pentachloride, niobium pentachloride, tantalum pentachloride, tin tetrachloride, or titanium tetrachloride. This halide may be a mixture of at least two halides.

In the invention, compositional change of the fluorination catalyst during the fluorination can effectively be prevented by treating, prior to the fluorination, the fluorination catalyst with a fluorination agent such as hydrogen fluoride, fluorohydrocarbon or fluorochlorohydrocarbon, at a temperature not lower than the reaction temperature of the fluorination. Once the fluorination catalyst activity is inactivated by the reaction, it is possible to reactivate the catalyst by bringing the inactivated catalyst into contact with an oxidative substance such as oxygen, air, ozone and chlorine. In some cases, it is preferable to continuously or intermittently supply to the reaction system an active substance, such as oxygen, ozone, chlorine, chlorine fluoride, chlorine trifluoride, nitrogen oxide, or nitrous oxide, in order to maintain the activity of the fluorination catalyst.

In the invention, the reaction temperature of the fluorination is preferably from about 100 to about 800° C. In the production of the first perhalogenated cyclopentene, it is preferably from about 100 to about 500° C., more preferably from 120 to 400° C., still more preferably from 120 to 300° C. In the production of the perhalogenated cyclopentane, it is preferably from about 150 to about 800° C., more preferably from 200 to 750° C., still more preferably from 250 to 700° C. If the reaction temperature is lower than the preferable lower limit (100° C. or 150° C.), the reaction rate may become too low and thus impractical. If the reaction temperature is too high, the reaction rate becomes high. This, however, causes the deterioration of the fluorination catalyst, and it is not economical, since it requires a large amount of heat energy.

In the invention, the molar ratio of the starting material, which is supplied to the reaction zone, to hydrogen fluoride may be in a range of $\frac{1}{100}$ to $\frac{1}{2}$ and may vary, depending on the type and composition of the starting material, the type and composition of the fluorinated product, and the reaction temperature. For example, if it is intended to obtain 1,2-dichlorohexafluorocyclopentene or 1,1-dichlorocyclopentane from perchlorocyclopentadiene or octachlorocyclopentene, the molar ratio is preferably from $\frac{1}{90}$ to $\frac{1}{5}$, more preferably from $\frac{1}{80}$ to $\frac{1}{10}$, still more preferably from $\frac{1}{60}$ to $\frac{1}{20}$. As another example, if it is intended to obtain 1,1-dichlorooctafluorocyclopentane from 1,2-dichlorohexafluorocyclopentene, the molar ratio is preferably from 1/30 to 1/2, more preferably from 1/20 to 1/3. It is preferable to suitably increase the amount of hydrogen fluoride relative to that of the starting material, in case that the fluorinated product is intended to have a higher degree of fluorination. If the amount of hydrogen fluoride is excessive, the production per unit time may become too low. On the other hand, if it is too small, conversion and yield may become too low.

In the invention, the amount of chlorine, which is supplied to the reaction system, is preferably at least 1 mol relative to 1 mol of the starting material. From the viewpoint of stoichiometry, the amount of chlorine required in the reaction depends on the type and the composition of the starting material. In fact, it is preferable to supply at least 1 mol of chlorine relative to 1 mol of the starting material in order to obtain a perhalogenated cyclopentene from a perhalogenated cyclopentadiene or obtain a perhalogenated cyclopentane from a perhalogenated cyclopentene. Furthermore, it is preferable to supply at least 2 moles of chlorine relative to 1 mol of the starting material in order to obtain a perhalogenated cyclopentane from a perhalogenated cyclopentadiene. Thus, the preferable lower limit of the chlorine supply is 1 mol or 2 moles relative to 1 mol of the starting material. The upper limit of the chlorine supply is preferably about 50 moles, more preferably 30 moles, still more preferably 10 moles, still further preferably 5 moles, relative to 1 mol of the starting material. Even if an excessive amount of chlorine is used, it does not interfere with the reaction. If the amount of chlorine is, however, so excessive, it may become cumbersome to treat the unreacted chlorine. It is possible to use an excessive amount of chlorine in case that a perhalogenated cyclopentane is intended as the fluorinated product of the reaction.

In the invention, the reaction pressure of the fluorination is not particularly limited. It is preferably from 1 to 10 kg/cm$^2$ in view of the selection of devices. It is preferable to choose a suitable reaction condition in which intermediate substances and hydrogen fluoride, which are present in the reaction system, do not essentially liquefy, that is, they are not present in the form of liquid drops. The contact time of the fluorination is preferably from 0.1 to 300 seconds, more preferably from 1 to 100 seconds, still more preferably from 2 to 50 seconds.

In the invention, a reactor used in the fluorination is preferably made of a material that is beat resistant and corrosion resistant against hydrogen fluoride, hydrogen chloride, chlorine and the like, such as stainless steel, Hastelloy, Monel metal or platinum, or a material lined with one of these metals. In the invention, the fluorinated product, that is, a mixture of the first perhalogenated cyclopentene and the perhalogenated cyclopentane, may be purified by a conventional purification process that is not particularly limited. In this process, for example, the reaction products, together with hydrogen chloride, the unreacted hydrogen fluoride and chlorine, are taken out of the reactor in the form of gas or liquid. Then, they are washed with water and/or a basic solution or subjected to a treatment such as distillation or liquid phase separation, to remove hydrogen chloride and an excessive amount of hydrogen fluoride. Then, the remaining acid substances are removed by a basic substance or the like, followed by rectification, thereby to obtain the first perhalogenated cyclopentene, the perhalogenated cyclopentane and the like.

After the above-mentioned fluorination (first fluorination) of the starting material to obtain a fluorinated product, it is optional to conduct a further fluorination (second fluorination) of this fluorinated product. If the second fluorination is conducted after the first fluorination, the above-mentioned rectification is not necessarily needed. In fact, in some cases, it may be only necessary between the first and second fluorinations to remove acid substances from the fluorinated products of the first fluorination. In other cases, even the removal of acid substances therefrom may not be necessary, but only the decrease of the acid content of the fluorinated products may be sufficient. If the fluorinated products of the first fluorination contain the unreacted raw materials and low-fluorinated products other than the aimed products, these substances can be used again in the first fluorination. Upon this reuse, according to need, it is possible to further fluorinate the perhalogenated cyclopentane. Alternatively, it is possible to conduct the second fluorination in order to further fluorinate the reaction products of the first fluorination into octafluorocyclopentene, decafluorocyclopentane and the like. The second fluorination is not limited to a particular fluorination, and it can be conducted under a severer condition than that of the first fluorination, for example, by increasing the reaction temperature and/or by increasing the molar ratio of hydrogen fluoride to the starting material. Alternatively, the second fluorination can be conducted in a reaction manner different from that of the first fluorination. For example, the second fluorination can be a fluorination in which chlorine atom of the reaction products of the first fluorination is replaced with fluorine atom of a metal fluoride. This metal fluoride is commonly used for fluorinating chlorinated alkanes and chlorinated alkenes. In the second fluorination, a mixture of the first perhalogenated cyclopentene and the perhalogenated cyclopentane can be fluorinated. The metal fluoride used in the second fluorination is not particularly limited, and may be an alkali metal fluoride, such as lithium fluoride, sodium fluoride, potassium fluoride, cesium fluoride or rubidium fluoride. Of these, potassium fluoride and cesium fluoride are preferable. The amount by mol of this metal fluoride is preferably at least D, more preferably from D to 10D, still more preferably from D to 5D, relative to 1 mol of the raw material of the second fluorination, that is, the first perhalogenated cyclopentene represented by the general formula $C_5Cl_DF_{8-D}$, where D is an integer of 2–7. Similarly, the amount by mol of the metal fluoride is preferably at least E, more preferably from E to 10E, still more preferably from E to 5E, relative to 1 mol of the raw material of the second fluorination, that is, the perhalogenated cyclopentane represented by the general formula $C_5Cl_EF_{10-E}$ where E is an integer of 2–9. According to need, it is optional to use a solvent in the second fluorination. Examples of this solvent are acid amides such as formamide, acetamide, N,N-dimethylformamide, N,N-dimethylacetamide and N-methylpyrrolidone, and sulfoxides such as dimethylsulfoxide and diethylsulfoxide. According to need, this solvent may be mixed with a hydrocarbon (e.g., xylene) that is compatible with the solvent. The reaction temperature of the second fluorination is preferably not higher than 200° C., more preferably from 60 to 180° C., still more preferably from 80 to 150° C. The reaction time of the second fluorination is suitably decided depending on the type of the metal fluoride of the second fluorination, and it may be up to 24 hr.

The following nonlimitative catalyst preparations are illustrative of the present invention.

CATALYST PREPARATION 1

At first, a 1-liter glass flask was charged with 100 g of a granular coconut husk activated carbon made by Takeda Chemical Industries, Ltd. having a trade name of GRANU- LAR SHIRO SAGI GX, which is made of columnar carbon grains having a size of 4–6 mesh screen, a surface area of 1,200 m²/g and a micropore diameter of 18Å. Then, the glass flask was heated to a temperature of 130–150° C., followed by the removal of steam by vacuum with a vacuum pump. At the time when it was found that steam flow therefrom stopped, it was started to introduce nitrogen into the flask to have normal pressure. With this, an activated carbon catalyst C-1 was prepared.

CATALYST PREPARATION 2

Catalyst Preparation 1 was repeated except in that the above activated carbon was replaced with (1) a granular coconut husk activated carbon made by Takeda Chemical Industries, Ltd. having a trade name of GRANULAR SHIRO SAGI CX, which is made of columnar carbon grains having a size of 4–6 mesh screen, (2) a granular coconut husk activated carbon made by Ohira Kagaku Sangyo Co. having a trade name of YASHICOL GX, which is made of columnar carbon grains having a size of 4–6 mesh screen, (3) a molecular sieving carbon made by Takeda Chemical Industries, Ltd. having a trade name of MOLSIEBON 5A, and (4) a granular coconut husk activated carbon made by Takeda Chemical Industries, Ltd. having a trade name of GRANULAR SHIRO SAGI G2X, which is made of columnar carbon grains having a size of 4–6 mesh screen, thereby to prepare catalysts C-2, C-3, C-4 and C-5, respectively.

CATALYST PREPARATION 3

At first, Catalyst Preparation 1 was repeated, thereby to obtain an activated carbon that is same as the catalyst C-1, in a 1-liter glass flask. Then, dried ethanol was added to this activated carbon in a manner to thoroughly soak the activated carbon therewith. Separately, a 500 ml glass flask was charged with 9.9 g of tantalum pentachloride, and then 200 ml of dried ethanol was added thereto. The resultant mixture was stirred to prepare a tantalum pentachloride solution. This solution was added to the 1-liter glass flask. The obtained mixture was stirred gently and then was allowed to stand still for 2 days. Then, the activated carbon was taken out of the flask and then dried in an evaporator. Then, the activated carbon was put into a cylindrical reaction tube that is equipped with an electric furnace and is made of stainless steel (SUS304) and has a diameter of 2.5 cm and an axial length of 40 cm. The reaction tube temperature was increased to 400° C., while nitrogen gas was allowed to flow therethrough. This condition was maintained for 4 hr. Then, the reaction tube temperature was decreased to room temperature, thereby to prepare a tantalum-carried activated carbon catalyst M-1.

CATALYST PREPARATION 4

Catalyst Preparation 3 was repeated except in that 9.9 g of tantalum pentachloride was replaced with 14.5 g of niobium pentachloride. With this, a niobium-carried activated carbon catalyst M-2 was prepared.

CATALYST PREPARATION 5

Catalyst Preparation 3 was repeated except in that 9.9 g of tantalum pentachloride was replaced with 14.3 g of molybdenum pentachloride. With this, a molybdenum-carried activated carbon catalyst M-3 was prepared.

CATALYST PREPARATION 6

At first, a granular coconut husk activated carbon that is the same as that of Catalyst Preparation 1 was dried at a temperature of 100–120° C. under reduced pressure. Then, 200 ml of the dried activated carbon was put into a 300 ml eggplant type flask. Then, 100 g of antimony pentachloride was dropped from a dropping funnel onto the activated carbon at a temperature of not higher than 50° C., while the flask was shaken sufficiently. Then, 200 ml of the obtained activated carbon carrying thereon antimony pentachloride was put into a cylindrical reaction tube that is the same as that of Catalyst Preparation 3. Then, the reaction tube temperature was gradually increased from room temperature to 150° C., while nitrogen was introduced thereinto at a rate of 1.2 liter/hr and hydrogen fluoride vaporized by a vaporizer connected to the reaction tube was introduced thereinto at a rate of 36 g/hr. This condition was maintained for 1 hr at 150° C. Then, the hydrogen fluoride flow was stopped, and then the reaction tube was decreased to room temperature. After that, the reaction tube temperature was gradually increased from room temperature to 150° C., while chlorine was introduced thereinto at a rate of 300 ml/hr. This condition was maintained for 1 hr at 150° C., thereby to prepare an antimony-carried activated carbon catalyst M-4.

CATALYST PREPARATION 7

At first, a 1-liter glass flask was charged with 100 g of a granular coconut husk activated carbon that is the same as that of Catalyst Preparation 1. Then, the flask was heated to a temperature of 130–150° C., and then steam was removed under reduced pressure with a vacuum pump. At the time when it was found that steam flow therefrom stopped, it was started to introduce nitrogen into the flask to have normal pressure. Then, dried ethanol was added to the activated carbon in a manner to thoroughly soak the activated carbon therewith. Separately, a 300 ml glass flask was charged with 100 g of pure water, followed by heating at 90° C. Then, 1.67 g of palladium chloride and 5 g of 35% hydrochloric acid were added thereto, followed by stirring to dissolve these substances. Then, an iron nitrate solution was added thereto, followed by stirring for 1 hr to prepare a solution. This solution was added to the 1-liter glass flask. The obtained mixture was stirred gently and then was allowed to stand still for 2 days. Then, the activated carbon was taken out of the flask and then dried in an evaporator. Then, the activated carbon was put into a cylindrical reaction tube that is the same as that of Catalyst Preparation 3. The reaction tube temperature was increased to 450° C., while nitrogen gas was allowed to flow therethrough. This condition was maintained for 4 hr. Then, the reaction tube temperature was decreased to room temperature, thereby to prepare an iron-and-palladium-carried activated carbon catalyst M-5.

CATALYST PREPARATION 8

At first, 800 g of an activated alumina, KHS-46 (trade name) of SUMITOMO CHEMICAL CO., LTD. having a particle diameter of 4–6 mm, was washed with water to remove powder from its surface. Separately, 306 g of hydrogen fluoride (anhydrous hydrofluoric acid) was dissolved in 2,760 g of water, to prepare a 10% hydrogen fluoride aqueous solution. Then, this solution was gradually poured onto the activated alumina, followed by stirring. After that, it was allowed to stand still for 3 hr, and then the activated alumina was taken out of the solution, then washed with water, then filtered, and then dried for 2 hr in an electric furnace at 200° C. The dried activated alumina in an amount of 800 ml was introduced into a stainless steel (SUS 304) cylindrical reaction tube having an inside diameter of 4.2 cm and an axial length of 60 cm. The temperature of the reaction tube was increased to 200° C. in the furnace, while nitrogen was allowed to flow through the reaction tube. Then, hydrogen fluoride, together with nitrogen, was allowed to flow therethrough, to fluorinate the activated alumina. As this fluorination proceeded, the temperature increased. However, the flow rates of nitrogen and hydrogen fluoride were suitably adjusted to make the temperature not higher than 400° C. After the heat generation terminated, the temperature of the furnace was maintained at 400° C. for 2 hr, thereby to prepare a fluorinated alumina.

Then, a 1-liter glass flask was charged with 200 g of the obtained fluorinated alumina. Then, dried ethanol was added to the fluorinated alumina in a manner to thoroughly soak the fluorinated alumina therewith. Separately, a 1-liter glass flask was charged with 29.1 g of niobium pentachloride, and then 400 ml of dried alcohol was added thereto. The resultant mixture was stirred to prepare a niobium pentachloride solution. This solution was added to the 1-liter glass flask containing the fluorinated alumina. The obtained mixture was stirred gently and then was allowed to stand still for 2 days. Then, the fluorinated alumina was taken out of the flask and then dried in an evaporator. Then, the activated carbon was put into a cylindrical reaction tube that is the same as that of Catalyst Preparation 3. The reaction tube temperature was increased to 400° C., while nitrogen gas was allowed to flow therethrough. This condition was maintained for 4 hr. Then, the reaction tube temperature was decreased to room temperature, thereby to prepare a niobium-carried fluorinated alumina catalyst M-6.

CATALYST PREPARATION 9

Catalyst Preparation 6 was repeated except in that the granular coconut husk activated carbon (GRANULAR SHIRO SAGI GX) was replaced with another granular coconut husk activated carbon made by Takeda Chemical Industries, Ltd. having a trade name of GRANULAR SHIRO SAGI G2X, which is made of columnar carbon grains having a size of 4–6 mesh screen. With this, an antimony-carried activated carbon catalyst M-7 was prepared.

The following nonlimitative examples are illustrative of the present invention. Hereinafter, abbreviations may be used for representing the following compounds:

1C9F-CPA: chlorononafluorocyclopentane;

1C7F-CPE: 1-chloroheptafluorocyclopentene;

2C8F-CPA: 1,1-dichlorooctafluorocyclopentane;

2C6F-CPE: 1,2-dichlorohexafluorocyclopentene;

3C7F-CPA: 1,1,2- trichloroheptafluorocyclopentane;

3C5F-CPE: trichloropentafluorocyclopentene;

4C6F-CPA: tetrachlorohexafluorocyclopentane;

4C4F-CPE: tetrachlorotetrafluorocyclopentene;

5C3F-CPE: pentachlorotrifluorocyclopentene;

8C-CPE: perchlorocyclopentene; and

6C-CPDE: perchlorocyclopentadiene.

EXAMPLE 1

At first, 180 ml of the gas phase fluorination catalyst (activated carbon catalyst C-1) prepared at Catalyst Preparation 1 was put in a cylindrical reaction tube that is the same as that of Catalyst Preparation 3. Then, while chlorine gas was allowed to flow therethrough at a rate of about 50 ml/min, the reaction tube temperature was gradually increased. When it reached 347° C., the flow rate of chlorine gas was changed from about 50 ml/min to 100 ml/min (6 liter/hr). Upon this, it was started to introduce each of hydrogen fluoride and 1,2-dichlorohexafluorocyclopentene (2C6F-CPE) into the reaction tube at a rate of 0.6 g/min (36 g/hr). About 10 hr after the start of the reaction, the reaction reached a steady state. Upon this, a gas component discharged from the reaction tube was analyzed by gas chromatography. With this, as shown in Table 1, it was found that the gas component contained 0.5% of 1C9F-CPA, 0.1% of 1C7F-CPE, 69.8% of 2C8F-CPA, 11.4% of 2C6F-CPE, 13.1% of 3C7F-CPA, and 1.7% of 3C5F-CPE. These percentages are areal percentages in chromatogram, and FID was used as detector of gas chromatography.

1,1-dichlorooctafluorocyclopentane: $^{19}$F-NMR

: –119.2 ppm(s, 4F), –122.5 ppm(s, 4F) (CC13F:0 ppm)

:13C-NMR:112.2 ppm, 110.3 ppm, 80.0 ppm (CDC13:77.0 ppm):MS(EI):282(M+), 263, 247, 228, 213, 197, 178, 163 (base peaks), 147, 131, 100.

TABLE 1

| | Catalyst | Reaction Temp. (° C.) | 2C6F-CPE Flow Rate (g/hr) | HF Flow Rate (g/hr) | Chlorine Flow Rate (l/hr) | Gas Component Composition (areal %) | | | | | |
|---|---|---|---|---|---|---|---|---|---|---|---|
| | | | | | | 1C9F-CPA | 1C7F-CPE | 2C8F-CPA | 2C6F-CPE | 3C7F-CPA | 3C5F-CPE |
| Ex. 1 | C-1 | 347 | 36 | 36 | 6.0 | 0.5 | 0.1 | 69.8 | 11.4 | 13.1 | 1.7 |
| Ex. 2 | C-1 | 333 | 48 | 48 | 6.0 | 0.1 | 0.1 | 70.2 | 13.4 | 12.6 | 1.6 |
| Ex. 3 | C-1 | 260 | 48 | 48 | 6.0 | — | 0.2 | 49.8 | 29.9 | 16.0 | 0.9 |
| Ex. 4 | C-2 | 330 | 48 | 48 | 6.0 | 0.1 | 0.7 | 74.1 | 10.8 | 11.6 | 1.0 |
| Ex. 5 | C-2 | 250 | 48 | 48 | 6.0 | 0.3 | 0.0 | 43.2 | 38.6 | 13.7 | 1.1 |
| Ex. 6 | C-3 | 336 | 48 | 48 | 6.0 | 0.1 | 0.1 | 69.4 | 14.0 | 12.7 | 1.8 |
| Ex. 7 | C-4 | 330 | 48 | 48 | 6.0 | 0.1 | 1.1 | 30.3 | 52.6 | 10.6 | 3.5 |
| Ex. 8 | M-1 | 330 | 24 | 24 | 4.8 | — | 0.1 | 63.0 | 20.0 | 13.7 | 2.0 |
| Ex. 9 | M-2 | 270 | 24 | 24 | 4.8 | — | 0.7 | 15.7 | 78.2 | 3.7 | 1.7 |
| Ex. 10 | M-2 | 400 | 24 | 24 | 4.8 | — | 0.9 | 33.8 | 53.5 | 7.4 | 3.3 |
| Ex. 11 | M-3 | 330 | 24 | 24 | 2.4 | — | 0.7 | 27.1 | 59.4 | 6.6 | 5.2 |
| Ex. 12 | M-3 | 330 | 24 | 24 | 4.8 | — | 0.7 | 27.8 | 57.7 | 7.7 | 4.6 |
| Ex. 13 | M-4 | 330 | 24 | 24 | 4.8 | — | 2.3 | 9.9 | 50.1 | 31.4 | 1.7 |
| Ex. 14 | M-5 | 400 | 24 | 24 | 4.8 | — | 2.1 | 20.7 | 65.5 | 7.2 | 4.2 |
| Ref. Ex. 1 | M-6 | 330 | 24 | 24 | 4.8 | — | 0.4 | 0.1 | 98.3 | — | 1.1 |
| Ref. Ex. 2 | M-3 | 330 | 24 | 24 | 0 | — | 13.4 | — | 86.3 | — | — |

EXAMPLES 2–14

In each of Examples 2–14, Example 1 was repeated except in that selective changes were made with respect to reaction conditions shown in Table 1. In each of Examples 2–14, the gas chromatographic analysis was conducted after a steady state was reached. Examples 2–14 were not the same, but within a range of 2–10 hr, with respect to the time from the start of the reaction to the steady state.

Referential Example 1

Example 1 was repeated except in that selective changes were made with respect to reaction conditions shown in Table 1 and that the gas chromatographic analysis was conducted 2 hr after the start of the reaction.

Referential Example 2

At first, 180 ml of the gas phase fluorination catalyst (activated carbon catalyst M-3) prepared at Catalyst Preparation 5 was put in a cylindrical reaction tube that is the same as that of Catalyst Preparation 3. Then, while nitrogen gas was allowed to flow therethrough at a rate of about 50 ml/min, the reaction tube temperature was gradually increased. When it reached 330° C., it was started to introduce each of hydrogen fluoride and 1,2-dichlorohexafluorocyclopentene into the reaction tube at a rate of 0.4 g/min (24 g/hr). About 5 hr after the start of the reaction, the reaction reached a steady state. Upon this, a gas component discharged from the reaction tube was analyzed by gas chromatography. The results are shown in Table 1.

EXAMPLE 15

At first, 100 ml of the gas phase fluorination catalyst (activated carbon catalyst M-7) prepared at Catalyst Preparation 9 was put in a cylindrical reaction tube that is the same as that of Catalyst Preparation 3. Then, the reaction tube temperature was gradually increased. When, it reached 50° C., it was started to introduce nitrogen, chlorine and hydrogen fluoride into the reaction tube at rates of 20 ml/min, 30 ml/min and 0.64 g/min, respectively. This hydrogen fluoride was vaporized by a vaporizer connected to an upper part of the reaction tube, prior to the introduction. When the reaction tube temperature reached 190° C., the nitrogen flow was stopped. Then, 77.9 g of hexachlorocyclopentadiene (6C-CPDE) and 164.0 g of hydrogen fluoride were supplied to the reaction tube by spending 4.25 hr. Then, a generated gas discharging from the reaction tube was collected by a trap having iced water. With this, 63.6 g of an organic matter was obtained. This organic matter was analyzed by gas chromatography and found to have a composition of 74.0% 2C6F-CPE, 0.2% 3C7F-CPA, 19.2% 3C5F-CPE, 4.2% 4C4F-CPE, and 0.3% 5C3F-CPE, as shown in Table 2.

EXAMPLE 16

At first, 100 ml of the gas phase fluorination catalyst (activated carbon catalyst M-7) prepared at Catalyst Preparation 9 was put in a cylindrical reaction tube that is the same as that of Catalyst Preparation 3. Then, the reaction tube temperature was gradually increased. When, it reached 50° C., it was started to introduce nitrogen, chlorine and hydrogen fluoride into the reaction tube at rates of 20 ml/min, 30 ml/mn and 0.75 g/min, respectively. This hydrogen fluoride was vaporized in the same manner as that of Example 15, prior to the introduction. When the reaction tube temperature reached 170° C., the nitrogen flow was stopped. Then, 78.6 g of hexachlorocyclopentadiene and 180.4 g of hydrogen fluoride were supplied to the reaction tube by spending 4 hr. Then, a generated gas discharging from the reaction tube was collected by a trap having iced water. With this, 61.8 g of an organic matter was obtained. This organic matter was analyzed by gas chromatography, and its results are shown in Table 2.

EXAMPLE 17

At first, 100 ml of the gas phase fluorination catalyst (activated carbon catalyst M-7) prepared at Catalyst Preparation 9 was put in a cylindrical reaction tube that is the same as that of Catalyst Preparation 3. Then, the reaction tube temperature was gradually increased. When, it reached 50° C., it was started to introduce nitrogen, chlorine and hydrogen fluoride into the reaction tube at rates of 20 ml/min, 50 ml/min and 0.62 g/min, respectively. This hydrogen fluoride was vaporized in the same manner as that of Example 15, prior to the introduction. When the reaction tube temperature reached 200° C., the nitrogen flow was stopped. Then, 64.9 g of hexachlorocyclopentadiene and 130.1 g of hydrogen fluoride were supplied to the reaction tube by spending 3.5 hr. Then, a generated gas discharging from the reaction tube was collected by a trap having iced water. With this, 55.3 g of an organic matter was obtained. This organic matter was analyzed by gas chromatography, and its results are shown in Table 2.

EXAMPLE 18

At first, 100 ml of the gas phase fluorination catalyst (activated carbon catalyst M-7) prepared at Catalyst Preparation 9 was put in a cylindrical reaction tube that is the same as that of Catalyst Preparation 3. Then, the reaction tube temperature was gradually increased. When, it reached 50° C., it was started to introduce nitrogen, chlorine and hydrogen fluoride into the reaction tube at rates of 20 ml/min, 60 ml/min and 0.72 g/min, respectively. This hydrogen fluoride was vaporized in the same manner as that of Example 15, prior to the introduction. When the reaction tube temperature reached 300° C., the nitrogen flow was stopped. Then, 37.8

TABLE 2

| | Catalyst | Reaction Temp. (° C.) | 6C-CPDE Flow Rate (g/hr) | HF Flow Rate (g/hr) | Chlorine Flow Rate (l/hr) | Collected Organic Matter Composition (areal %) | | | | | | |
|---|---|---|---|---|---|---|---|---|---|---|---|---|
| | | | | | | 1C7F-CPE | 2C8F-CPA | 2C6F-CPE | 3C7F-CPA | 3C5F-CPE | 4C4F-CPE | 5C3F-CPE |
| Ex. 15 | M-7 | 190 | 18.3 | 38.6 | 1.8 | — | — | 74.0 | 0.2 | 19.2 | 4.2 | 0.3 |
| Ex. 16 | M-7 | 170 | 19.7 | 45.1 | 1.8 | — | — | 63.8 | 0.3 | 27.4 | 6.8 | 0.5 |
| Ex. 17 | M-7 | 200 | 18.5 | 37.2 | 3.0 | — | — | 77.0 | 0.4 | 16.3 | 3.6 | 0.2 |
| Ex. 18 | M-7 | 300 | 18.9 | 43.3 | 3.6 | 0.7 | 0.3 | 69.8 | 1.3 | 14.9 | 3.4 | 0.4 | g of hexachlorocyclopentadiene and 86.5 g of hydrogen fluoride were supplied to the reaction tube by spending 2 hr. Then, a generated gas discharging from the reaction tube was collected by a trap having iced water. With this, 32.0 g of an organic matter was obtained. This organic matter was analyzed by gas chromatography, and its results are shown in Table 2.

EXAMPLE 19

At first, 200 ml of the gas phase fluorination catalyst (activated carbon catalyst C-5) prepared at Catalyst Preparation 2 was put in a cylindrical reaction tube that is the same as that of Catalyst Preparation 3. Then, while chlorine gas was allowed to flow therethrough at a rate of about 50 ml/min, the reaction tube temperature was gradually increased. When it reached about 340° C., the flow rate of chlorine gas was changed from about 50 ml/min to 100 ml/min (6 liter/hr). Upon this, it was started to introduce hydrogen fluoride and perchlorocyclopentene (starting material) into the reaction tube at rates of 0.6 g/min (36 g/hr) and 0.4 g/min (24 g/hr), respectively. About 10 hr after the start of the reaction, the reaction reached a steady state. Upon this, a gas component discharged from the reaction tube was analyzed by gas chromatography. With this, as shown in Table 3, it was found that the gas component contained 33.3% 2C8F-CPA, 32.7% 2C6F-CPE, 23.0% 3C7F-CPA, 7.4% 3C5F-CPE, 2.3% 4C4F-CPA, and 0.9% 4C4F-CPE.

EXAMPLES 22–23

In each of Examples 22–23, Example 19 was repeated except in that selective changes were made with respect to reaction conditions shown in Table 3. In fact, a mixture of perhalogenated cyclopentenes and perhalogenated cyclopentanes was used as the starting material (organic raw material). This mixture bad a composition of 29.8% 2C8F-CPA, 21.8% 2C6F-CPE, 20.6% 3C7F-CPA, 8.3% 3C5F-CPE, 9.1% 4C6F-CPA, 3.0% 4C4F-CPE and 7.4% of others. In each of these examples, the gas chromatographic analysis was conducted after a steady state was reached.

EXAMPLE 24

At first, 200 ml of the gas phase fluorination catalyst (activated carbon catalyst C-5) prepared at Catalyst Preparation 2 was put in a cylindrical reaction tube that is the same as that of Catalyst Preparation 3. Then, the reaction tube temperature was gradually increased. When, it reached 50° C., it was started to introduce nitrogen, chlorine and hydrogen fluoride into the reaction tube at rates of 20 ml/min, 70 ml/min and 40 g/hr, respectively. This hydrogen fluoride was vaporized by a vaporizer connected to an upper part of the reaction tube, prior to the introduction. When the reaction tube temperature reached about 340° C., the nitrogen flow was stopped. Then, 77.9 g of hexachlorocyclopentadiene (6C-CPDE) and 164.0 g of hydrogen fluoride were supplied

TABLE 3

| | Catalyst | Reaction Temp. (° C.) | Starting Material Flow Rate (g/hr) | HF Flow Rate (g/hr) | Chlorine Flow Rate (l/hr) | Gas Component Composition (areal %) | | | | | | |
|---|---|---|---|---|---|---|---|---|---|---|---|---|
| | | | | | | 1C7F-CPE | 2C8F-CPA | 2C6F-CPE | 3C7F-CPA | 3C5F-CPE | 4C6F-CPA | 4C4F-CPE |
| Ex. 19 | C-5 | 330 | 24 | 36 | 6 | — | 33.3 | 32.7 | 23.0 | 7.4 | 2.3 | 0.9 |
| Ex. 20 | C-5 | 330 | 12 | 36 | 6 | — | 59.7 | 9.2 | 20.2 | 3.8 | 3.9 | 0.0 |
| Ex. 21 | C-5 | 280 | 12 | 36 | 6 | — | 40.4 | 11.2 | 34.1 | 3.6 | 4.8 | 1.6 |
| Ex. 22 | C-5 | 330 | 12 | 36 | 18 | 0.4 | 79.7 | 0.5 | 9.5 | 1.7 | 5.3 | 1.1 |
| Ex. 23 | C-5 | 330 | 12 | 36 | 1.2 | 3.5 | 84.5 | 1.2 | 5.3 | 0.5 | 2.9 | 0.5 |

EXAMPLES 20–21

In each of Examples 20–21, Example 19 was repeated except in that selective changes were made with respect to reaction conditions shown in Table 3. In fact, perchlorocyclopentene was used as the starting material in each of Examples 20–21, too. In each of these examples, the gas chromatographic analysis was conducted after a steady state was reached.

to the reaction tube by spending 4.25 hr at rates of 16.2 g/hr and 50.4 g/hr, respectively. Then, a generated gas discharging from the reaction tube was collected by a trap having iced water. With this, 59.1 g of an organic matter was obtained. This organic matter was analyzed by gas chromatography and found to have a composition of 0.1% 1C7F-CPE, 44.7% 2C8F-CPA, 27.7% 2C6F-CPE, 16.1% 3C7F-CPA, 6.3% 3C5F-CPE, 1.8% 4C4F-CPA, and 1.7% 4C4F-CPE, as shown in Table 4.

TABLE 4

| | Catalyst | Reaction Temp. (° C.) | 6C-CPDE Flow Rate (g/hr) | HF Flow Rate (g/hr) | Chlorine Flow Rate (l/hr) | Gas Component Composition (areal %) | | | | | | |
|---|---|---|---|---|---|---|---|---|---|---|---|---|
| | | | | | | 1C7F-CPE | 2C8F-CPA | 2C6F-CPE | 3C7F-CPA | 3C5F-CPE | 4C6F-CPA | 4C4F-CPE |
| Ex. 24 | G-5 | 320 | 16.2 | 50.4 | 4.2 | 0.1 | 44.7 | 27.7 | i6.1 | 6.3 | 1.8 | 1.7 |
| Ex. 25 | C-5 | 320 | 21.0 | 40.2 | 2.0 | 0.2 | 12.7 | 64.0 | 6.4 | 11.3 | 1.2 | 2.2 |
| Ex. 26 | C-5 | 275 | 19.2 | 39.0 | 1.8 | 0.3 | 5.6 | 49.5 | 6.4 | 26.8 | 2.0 | 6.5 |
| Ex. 27 | C-5 | 280 | 18.6 | 40.8 | 4.2 | 0.1 | 3.9 | 24.2 | 13.3 | 24.9 | 8.4 | 15.9 |
| Ex. 28 | G-5 | 320 | 19.2 | 41.4 | 4.2 | 0.1 | 27.6 | 37.8 | 14.6 | 8.4 | 3.0 | 4.3 |

EXAMPLES 25–28

In each of Examples 25–28, Example 24 was repeated except in that selective changes were made with respect to reaction conditions shown in Table 4. In each of Examples 25–28, the gas chromatographic analysis was conducted after a steady state was reached. Examples 25–28 were not the same, but within a range of 2–10 hr, with respect to the time from the start of the reaction to the steady state.

The entire disclosure of each of Japanese Patent Application Nos. 10-314661 filed on Nov. 5, 1998 and 10-339420 filed on Nov. 30, 1998, of which priorities are claimed in the present application, including specification, claims, and summary, is incorporated herein by reference in its entirety.

What is claimed is:

1. A method for preparing a fluorinated product that is a first perhalogenated five-membered cyclic compound, said method comprising:
   reacting in a gas phase a starting material that is a second perhalogenated five-membered cyclic compound having at least one unsaturated bond, at substantially the same time with chlorine and hydrogen fluoride, in the presence of a fluorination catalyst comprising an activated carbon optionally carrying thereon a metal compound, thereby to decrease the number of said at least one unsaturated bond and to increase the number of fluorine atoms of said second compound.

2. A method according to claim 1, wherein said activated carbon carries thereon said metal compound containing at least one metal selected from metals of 4, 5, 6, 7, 9, 10, 11, 14 and 15 groups of periodic table.

3. A method according to claim 2, wherein said at least one metal is selected from manganese, cobalt, nickel, molybdenum, niobium, copper, antimony, titanium, tin and tantalum.

4. A method according to claim 3, wherein said at least one metal is selected from the group consisting of antimony, molybdenum, niobium, and tantalum.

5. A method according to claim 1, wherein said activated carbon carries thereon said metal compound that is at least one selected from the group consisting of antimony halides, molybdenum halides, niobium halides, and tantalum halides.

6. A method according to claim 5, wherein said metal compound is antimony pentachloride.

7. A method according to claim 1, wherein said activated carbon does not carry thereon said metal compound.

8. A method according to claim 5, wherein said activated carbon has a surface area of at least 400 m$^2$/g and a micropore volume of at least 0.1 cm$^3$/g.

9. A method according to claim 1, wherein said fluorinated product is a first perhalogenated cyclopentene represented by the general formula $C_5Cl_DF_{8-D}$, where D is an integer of 0–7, or a perhalogenated cyclopentane represented by the general formula $C_5Cl_EF_{10-E}$, where E is an integer of 0–9, and wherein said starting material is a perhalogenated cyclopentadiene represented by the general formula $C_5Cl_AF_{6-A}$, where A is an integer of 0–6, or a second perhalogenated cyclopentene represented by the general formula $C_5Cl_BF_{8-B}$, where B is an integer of 0–8.

10. A method according to claim 9, wherein said fluorinated product is said first perhalogenated cyclopentene represented by the general formula $C_5Cl_AF_{8-D}$, and said starting material is said perhalogenated cyclopentadiene represented by the general formula $C_5Cl_AF_{6-A}$, where said integers A and D are such that the expression D<(2+A) is satisfied.

11. A method according to claim 9, wherein said fluorinated product is said perhalogenated cyclopentane represented by the general formula $C_5Cl_EF_{10-E}$, and said starting material is said perhalogenated cyclopentadiene represented by the general formula $C_5Cl_AF_{6-A}$, where said integers A and E are such that the expression E<(4+A) is satisfied.

12. A method according to claim 9, wherein said fluorinated product is said perhalogenated cyclopentane represented by the general formula $C_5Cl_EF_{10-E}$, and said starting material is said second perhalogenated cyclopentene represented by the general formula $C_5Cl_BF_{8-B}$, where said integers B and E are such that the expression E<(2+B) is satisfied.

13. A method according to claim 9, wherein said starting material is hexachlorocyclopentadiene.

14. A method according claim 13, wherein said fluorinated product is 1,2-dichlorohexafluorocyclopentene, 1,2,4-trichloropentafluorocyclopentene, 1,2,3-trichloropentafluorocyclopentene, 1,2,3,4-tetrachlorotetrafluorocyclopentene, 1,1,2,2-tetrachlorohexafluorocyclopentane, 1,1,2-trichloroheptafluorocyclopentane, 1,1-dichlorooctafluorocyclopentane, 1,2-dichlorooctafluorocyclopentane, chlorononafluorocyclopentane, or decafluorocyclopentane.

15. A method according to claim 13, wherein said fluorinated product is 1,2-dichlorohexafluorocyclopentene.

16. A method according to claim 13, wherein said fluorinated product is 1,1-dichlorooctafluorocyclopentane.

17. A method according to claim 9, wherein said fluorinated product is octachlorocyclopentene or 1,2-dichlorohexafluorocyclopentene.

18. A method according to claim 17, wherein said fluorinated product is 1,1,2,2-tetrachlorohexafluorocyclopentane, 1,1,2-trichloroheptafluorocyclopentane, 1,1-dichlorooctafluorocyclopentane, 1,2-dichlorooctafluorocyclopentane, chlorononafluorocyclopentane, or decafluorocyclopentane.

19. A method according to claim 17, wherein said fluorinated product is 1,1-dichlorooctafluorocyclopentane.

20. A method according to claim 1, wherein said starting material is a perhalogenated cyclopentadiene represented by the general formula $C_5Cl_AF_{6-A}$, where A is an integer of 0–6, or a perhalogenated cyclopentene represented by the general formula $C_5Cl_BF_{8-B}$, where B is an integer of 0–8, and wherein said reacting is conducted at a reaction temperature of 100–800° C., under a reaction pressure of 1–10 kg/cm$^2$, with a contact time of 0.1–300 seconds, for which said starting material is in contact with said chlorine and said hydrogen fluoride, under a condition that a molar ratio of said hydrogen fluoride to said starting material is from 2 to 100 and that a molar ratio of said chlorine to said starting material is from 1 to 50.

21. A method according to claim 1, wherein said chlorine is in an amount of at least 1 mol relative to 1 mol of said starting material.

* * * * *